United States Patent [19]
Jordan et al.

[11] Patent Number: 5,402,228
[45] Date of Patent: Mar. 28, 1995

[54] ON-LINE DIRT COUNTER

[75] Inventors: Byron D. Jordan, Pointe Claire; Nam G. Nguyen, Montreal, both of Canada

[73] Assignee: Pulp and Paper Research Institute of Canada, Pointe Claire, Canada

[21] Appl. No.: 938,034

[22] PCT Filed: May 23, 1990

[86] PCT No.: PCT/CA90/00168
 § 371 Date: Oct. 28, 1992
 § 102(e) Date: Oct. 28, 1992

[87] PCT Pub. No.: WO91/18281
 PCT Pub. Date: Nov. 28, 1991

[51] Int. Cl.⁶ .................. G01N 21/88; G01N 21/86
[52] U.S. Cl. .................................................. 356/340
[58] Field of Search ................... 356/430, 237, 446; 250/576

[56] References Cited

U.S. PATENT DOCUMENTS

| | | |
|---|---|---|
| 3,883,436 | 5/1975 | Fletcher .................. 250/566 |
| 4,172,666 | 10/1979 | Clarke . |
| 4,226,541 | 10/1980 | Tisue .................. 356/446 |
| 4,237,539 | 12/1980 | Piovoso et al. . |
| 4,253,768 | 3/1981 | Yaroshuk et al. . |
| 4,665,317 | 5/1987 | Ferriere et al. . |
| 4,724,481 | 2/1988 | Nishioka . |
| 4,740,079 | 4/1988 | Koizumi et al. . |
| 4,794,264 | 12/1988 | Quackenbos et al. . |
| 4,794,265 | 12/1988 | Quackenbos et al. . |

FOREIGN PATENT DOCUMENTS 2549327  1/1985  France .

*Primary Examiner*—Richard A. Rosenberger

[57] ABSTRACT

The two-dimensional medium-pass filter principle is used to acquire a sharpened image initially In practice the sharpened image is obtained from the difference of a linear array signal of a partially out-of-focus image from another linear array signal of the same image but in focus. Integrated intensity of dirt specks higher than a user selected threshold are measured and accumulated. Each integrated intensity value is converted into its corresponding speck size with the use of a predefined fined look-up table. The counter generates a dirt speck histogram and statistical data within a preselected time interval or area coverage.

18 Claims, 4 Drawing Sheets

ON-LINE DIRT COUNTER

TECHNICAL FIELD

The invention relates to a dirt counter for measuring and recording dirt speck sizes and intensities on paper. More specifically, the invention relates to an on-line dirt counter which measures the dirt speck sizes and intensities on a surface of a web of moving paper.

BACKGROUND ART

Several off-line dirt counters have been developed. A typical one, such as the BIOTRAN TM (of New Brunswick Scientific) extracts measurements such as total area and total counts from two-dimensional incoming images. Recently, an off-line system PAPRICAN MICROSCANNER TM (of Noram Quality Control and Research Equipment Ltd.) image analyzer applies the medium-pass filter as well as visual impact principles to detect and measure dirt speck size of two-dimensional images. The INTEC TM (of Intec Corp.) on-line dirt counter uses a laser light source and fiber optic receivers. It can detect dirt specks as small as 0.05 mm$^2$. However, this device is not designed to measure dirt speck size using visual impact principles similar to human judgment as defined in TAPPI (Technical Association of the Pulp and Paper Industry) count.

There are also issued patents of interest which deal with the detection of flaws on surfaces. U.S. Pat. No. 4,172,666, Clarke, Oct. 30, 1979 distinguishes between different types of faults detected on a moving web. A defect detector scans the surface of the web with a laser and views the reflected light with a view or several detectors at various angles. Sums and differences between signals are used to discern which defects scatter light and which absorb it. The signal processing is not specifically related to the emulation of visual inspection as is the present invention.

U.S. Pat. Nos. 4,794,264 and 4,794,265, Quackenbos et al, Dec. 27, 1988, relate to an apparatus and method for uniquely detecting pits on a smooth surface. The moving surface is illuminated with a point source of laser light through a pair of beam splitters. Flaws and pits reflect specularly with different patterns. An annular mask shields one detector to view the neighborhood of a focal point and a window on the other detector constrains the signal to the central focus.

The invention in the above patents uses a beam splitter to view the same spot with a pair of detectors and to difference a central spot signal with a wider surround. However, Quackenbos et al illuminate the sample with a laser through the same beam splitter in order to observe glossy specular reflectance but does not illuminate diffusely outside the beam splitter to observe the fuse reflectance. Further, Quackenbos et al use a single detector in each beam rather than a linear array of detectors, and Quackenbos et al mask the two detectors to see only their intended domains of view rather than having the two beams differ only in sharpness of focus. Finally, Quackenbos et al use the difference of detector signals to distinguish flaws from pits but does not have a system wherein the signal differences correspond to a sharpening operation.

U.S. Pat. No. 4,740,079, Koizumi et al, Apr. 26, 1988, teaches a method and apparatus for detecting foreign substances, e.g. dirt specks or smudges, on the glossy surface of a semi-conductor chip which already contains delivered etches of the circuit. In the Koizumi et al patent, a circuit component is illuminated at near grazing incidence with a laser or a pair of lasers as the chip is physically moved past the detection configuration. A beam splitter divides the View of the surface of the chip in two identical beams with different polarization. Each beam is viewed at the same focus by a linear array of detectors. The difference signal corresponds to the diffused scattering from dirt on the chip. However, Koizumi et al does not calculate the integrated optical density as a visual impact parameter.

U.S. Pat. No. 4,724,481, Nishioka, Feb. 9, 1988, teaches a flaw detector for detecting a flaw in a sheet. The apparatus includes an array camera or series of array cameras which view a moving sheet. A circuit employs an electronic shading correction to enhance the signal to noise ratio. A memory associated with each photodetection element is used to maintain a reference level for that element. The novelty of this patent appears to reside in the algorithm of shading correction and data reduction. However, the Nishioka invention cannot be used on paper sheets with realistic reflectance nonuniformity associated with formation.

U.S. Pat. No. 4,237,539, Piovoso et al, Dec. 2, 1980, teaches an on-line web inspection system which includes a transverse web scanning means. X-ray film is made at high speeds and must be inspected for defects at speeds of up to 900 feet per minute. In the '539 patent, a flying spot crisscrosses crosses the sheet with a scan repeat of 1.5 mm. This requires three scans per millisecond. A sophisticated processing board in the host computer processes the signal and sorts features with sharp edges by size. In the '539 patent, a scanning laser is used rather than a diode array. In addition, the '539 patent does not use a board level processing of the signal to extract and sort the images of the defects. Instead, sorting is accomplished by area and by the sharpness of the edge of the feature, for example, rather than by integration of the signal strength within the bounds of a spot.

A system for detecting and classifying flaws on metallic surfaces is taught in U.S. Pat. No. 4,253,768, Yaroshuk et al, Mar. 3, 1981. In the '768 patent, a scanning laser illuminates a moving surface of, for example, a pipe, which is viewed by at least two detectors. The reflectance angles for the detectors are chosen so that most of the light reflects into the first detector when there are no defects with a low but finite intensity reaching the other detectors. The other detectors are positioned to receive increased intensity when the laser beam traverses a defect. The average signal serves as a base line for comparisons. This system has, of course, very little in common with systems for detecting dirt specks on a sheet of paper, and especially the system herein.

A particle detection method and system, for scanning the surface of a semi-conducting wafer, is taught in U.S. Pat. No. 4,766,324, Saadat et al, Aug. 23, 1988. The surfaces scanned by a laser beam, and the scattered light indicates the presence of a dirt speck. The central idea of this patent is a procedure for identification of dirt that was already present before the current processing step, and to distinguish this from dirt added by the most recent step. Once again, this has little in common with a dirt counter for measuring dirt speck sizes on a web of moving paper.

U.S. Pat. No. 4,665,317, Ferriere et al, May 12, 1987, teaches a process and equipment for sensing surface defects on a moving strip of rolled metal. Successive video images of a moving sheet of the metal are presented to a computer memory as a continuous representation of the surface. Two-dimensional digital filters are used for contour detection and the edge detection of defects. The method makes successive demands upon the host computer although the algorithms are quite general. This system bears, again, no resemblance to the system of the present application which does not use two-dimensional filters.

DISCLOSURE OF THE INVENTION

It is an object of the invention to provide an on-line dirt counter for measuring and recording dirt speck sizes and intensities on a first surface of a web of moving paper.

It is a more specific object of the invention to provide such a counter which includes a light source disposed to reflect light off the first surface of the web of moving paper.

It is a still more specific object of the invention to provide such a counter wherein the reflected light is split by a beam splitter, one of the split beams being directed to an out-of-focus detector, the other one of the spit beams being directed to an in-focus detector.

It is a still further object of the invention to provide such a counter wherein the reading of the sensor of the out-of-focus split beam is subtracted from the reading of the sensor of the in-focus split beam.

In accordance with the invention there is provided an on-line dirt counter for measuring and recording dirt speck sizes and intensities which appear on a first surface of a web of moving paper, comprising:
- a light source spaced from said first surface of said web of moving paper for directing a beam of light at said first surface of said web of moving paper, said beam of light being reflected from said first surface of said web of moving paper;
- a beam splitter spaced from said first surface of said web of moving paper to receive said reflected beam and to provide a first split beam, travelling in a first direction, and a second split beam, travelling in a second direction different from said first direction;
- an in-focus sensor means placed to receive said first split beam and to provide an in-focus signal having an in-focus magnitude proportional to the magnitude of the light intensity of said first split beam;
- an out-of-focus sensor means placed to receive said second split beam and to provide an out-of-focus signal having an out-of-focus magnitude proportional to the magnitude of the light intensity of said second split beam;
- means for subtracting said out-of-focus magnitude from said in-focus magnitude to provide a difference magnitude;
- means for providing a threshold signal having a threshold value proportional to a threshold intensity level;
- comparator means for comparing said difference magnitude to said threshold magnitude; and
- means for storing the occurrences and magnitudes of said difference magnitude on all occasions when said difference magnitude is greater than said threshold magnitude.

BRIEF DESCRIPTION OF DRAWINGS

The invention will be better understood by an examination of the following description, together with the accompanying drawings, in which.

DESCRIPTION OF PREFERRED EMBODIMENTS

It is the purpose of the present invention to provide an on-line dirt counter device to handle dirt speck detection and speck size estimation in the same manner as human judgment described in TAPPI count procedures. A discussion of the principles involved, without a description of specific apparatus or method steps, is given in "Emulating the TAPPI Dirt Count with a Microcomputer", Jordan et al, Journal of Pulp and Paper Science, Vol. 14, No. 1, January 1988, pps J16 to J19.

For dirt speck detection, any potential specks are detected whenever their contrast to neighboring background is higher than a predetermined threshold. A contrast image can be derived from an original image by applying a two-dimensional medium-pass filter. This is equivalent to extracting the difference between an original image and its corresponding out-of-focus one. Using two camera, for example, charge coupled device linear arrays, one viewing a paper portion in focus and the other viewing the same portion, but partially out of focus, a contrast image can be obtained from the difference of the two linear array signals. Any clusters of picture elements of the contrast image with their digitized values higher than a predetermined threshold are considered as dirt specks.

Integrated contrast values of the detected dirt specks are measured and stored. After a predetermined time interval, or a predetermined paper area coverage, all stored dirt speck integrated values are retrieved, converted into corresponding sizes by a precalculated look-up table, and accumulated in a dirt speck histogram. The look-up table can be constructed from graphs similar to that shown at FIG. 3 of Jordan et al referred to supra.

Accumulated statistical data and histograms can be reported regularly in a specific time interval until the paper roll is exhausted, or upon receipt of an operator hault request. At this point, all data are reset for preparing measurements of a new paper roll.

Figure 1:
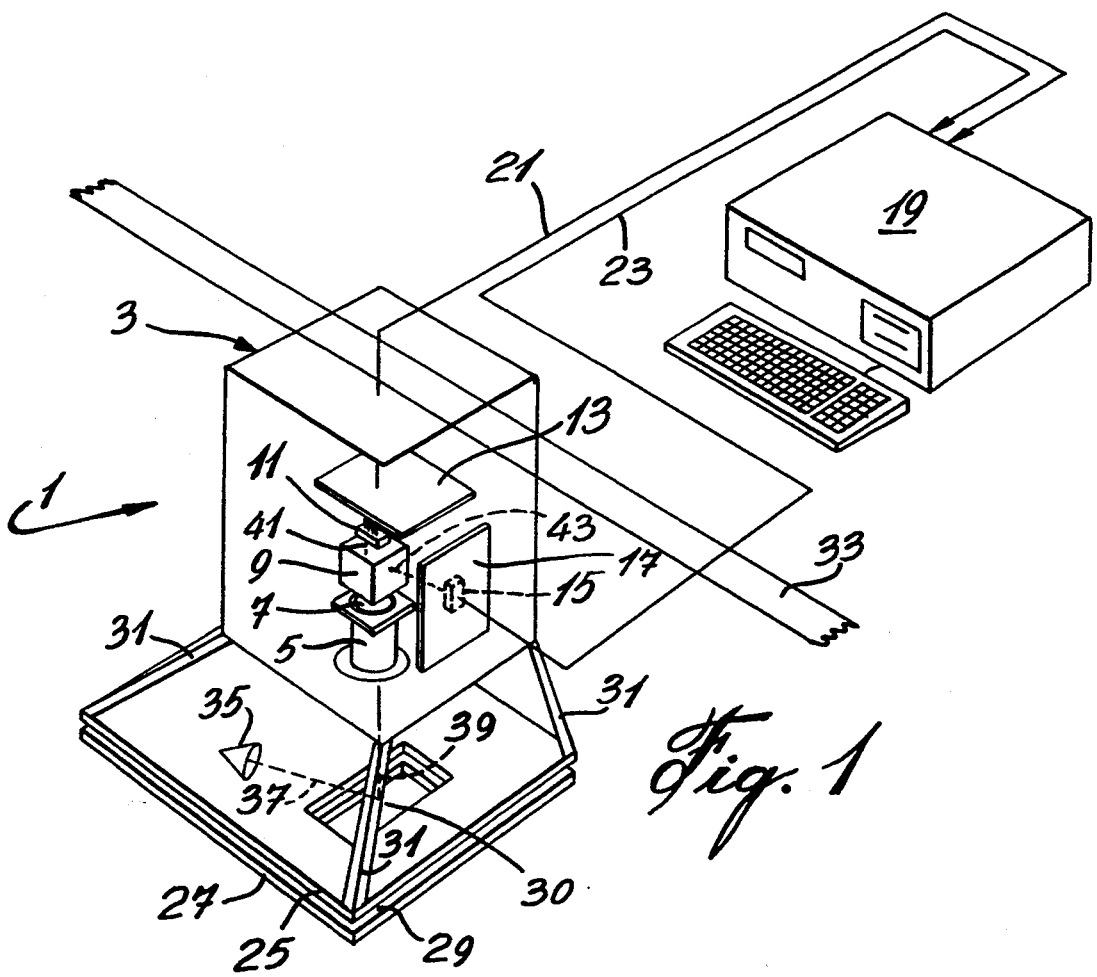
FIG. 1 is a perspective view of a dirt counter in accordance with the invention.

Referring to FIG. 1, the counter, illustrated generally at 1, comprises a housing 3. Disposed within the housing is a light guide 5 which guides light, as will be described below, to a focussing lens 7. After passing through the lens, the light is directed to a beam splitter 9 which directs one beam of light at an out-of-focus camera, for example, a CCD (charge couple device) sensor linear array 11 which is supported by a plate 13. The other split beam of light is directed at an in-focus camera, for example, a CCD sensor linear array 15 which is supported on a plate 17.

The outputs of sensors 11 and 15 are fed to processor 19 via buses 21 and 23 respectively.

Spaced from the housing 3 (in the illustrated example, underlying the housing 3) are paper guiding means comprising spaced stabilizer plates 25 and 27 having a space 29 between them. A web of paper to be tested moves in the machine direction, illustrated by the arrow A, in the space between the stabilizer plates. The means for guiding the paper is physically connected to the housing, to move with the housing as will be described below, by beams 31.

Figure 1A:
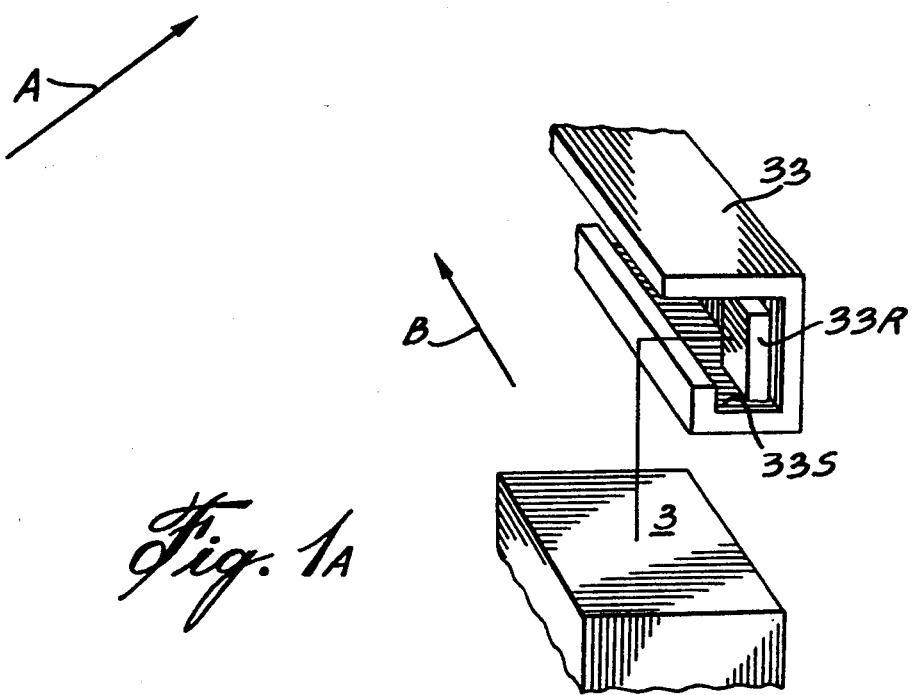
FIG. 1A illustrates a possible arrangement for driving the housing in a cross-machine direction.

The housing 33 moves in a cross-machine direction, illustrated by arrow B, along the rail 33 using means well known in the art. For example, as illustrated in FIG. 1A, housing 3 can be attached to a roller 3R which is guided for movement in the cross-machine direction by slot 33S in rail 33. The roller would be driven by a motor as is well known in the art.

A light source 35 is disposed to direct a beam of light 37 to one surface of the web of moving paper (in the illustrated embodiment, the top surface). The beam 37 is reflected by the surface of the web of moving paper to provide a reflected beam 39 which is received by the light guide 5. The light guide 5 directs the beam 39 to the focussing lens 7 which in turn directs the focus beam to beam splitter 9.

Beam splitter 9 provides a first split beam 41, directed at the out-of-focus CCD sensor 11, and a second split beam 43, directed at the in-focus CCD sensor 15.

The output signals of the sensors 11 and 15 are transmitted to a data analysis board, which is not illustrated in FIG. 1, but which is installed in the processor 19.

Figure 2:
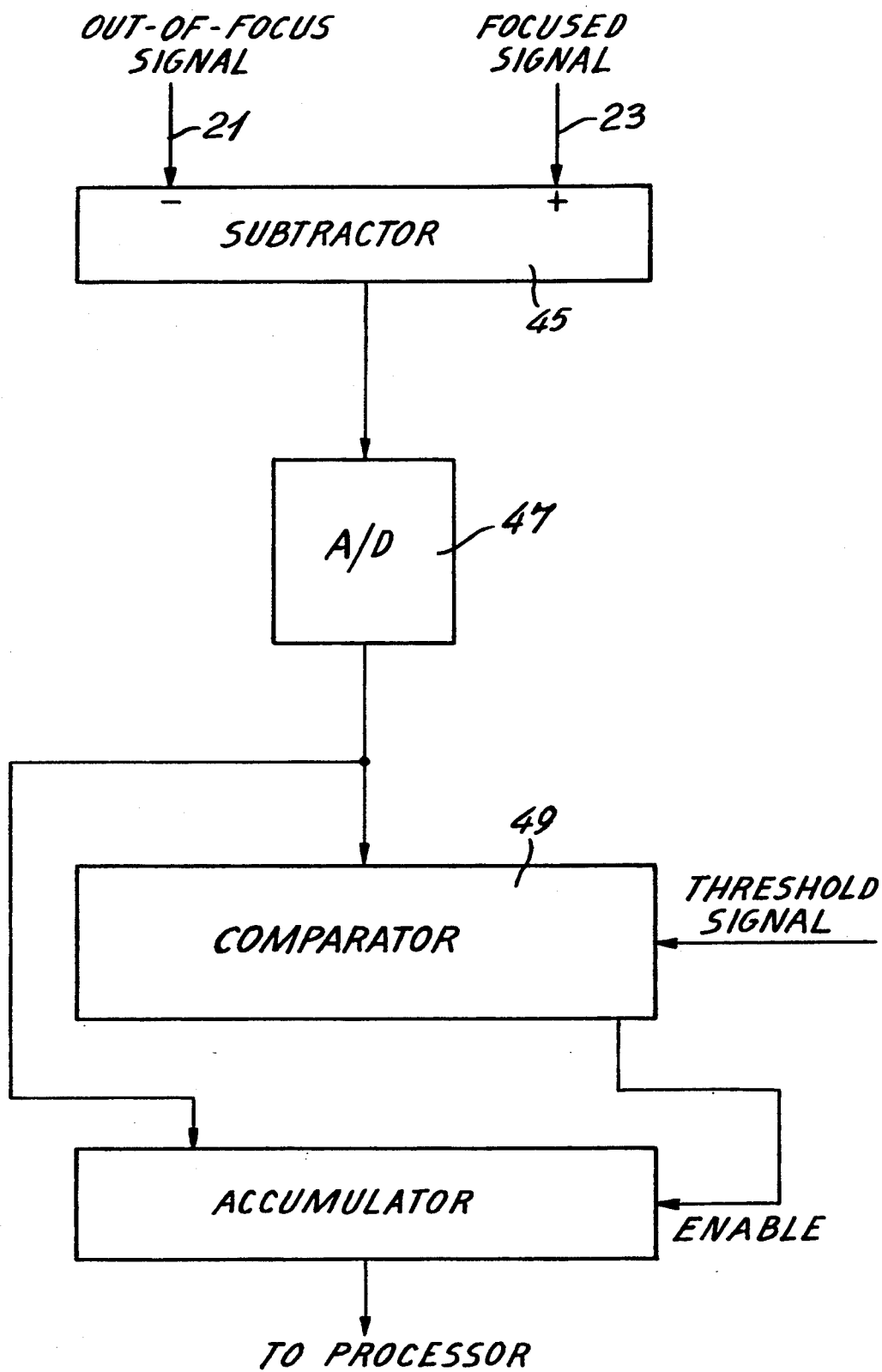
FIG. 2 is a schematic view of the data analysis board.

Referring to FIG. 2, the data analysis board comprises a subtractor 45 having its positive input terminal fed with the in-focus signal and its negative input terminal fed with the out-of-focus signal. The sum of the focus signal less the out-of-focus signal is fed to analog-to-digital converter 47 whose output is fed to one input of a comparator 49. The second input of the comparator 49 is fed a predetermined threshold signal.

The output of the comparator 49 is fed to an enable terminal of accumulator 51, and the output of the analog-to-digital converter 47 is fed, in parallel, to the data input terminal of accumulator 51. The output of accumulator 51 is fed to the processor.

In operation, and referring first to FIG. 1, the dirt counter works as follows:

The reflected light 39 is guided, by guide 5, to the lens 7 where it is focussed and applied to beam splitter 9. The beam splitter 9 directs a first split beam 41 to the out-of-focus sensor 11, and a second split beam, 43, to the in-focus sensor 15.

Figure 3:
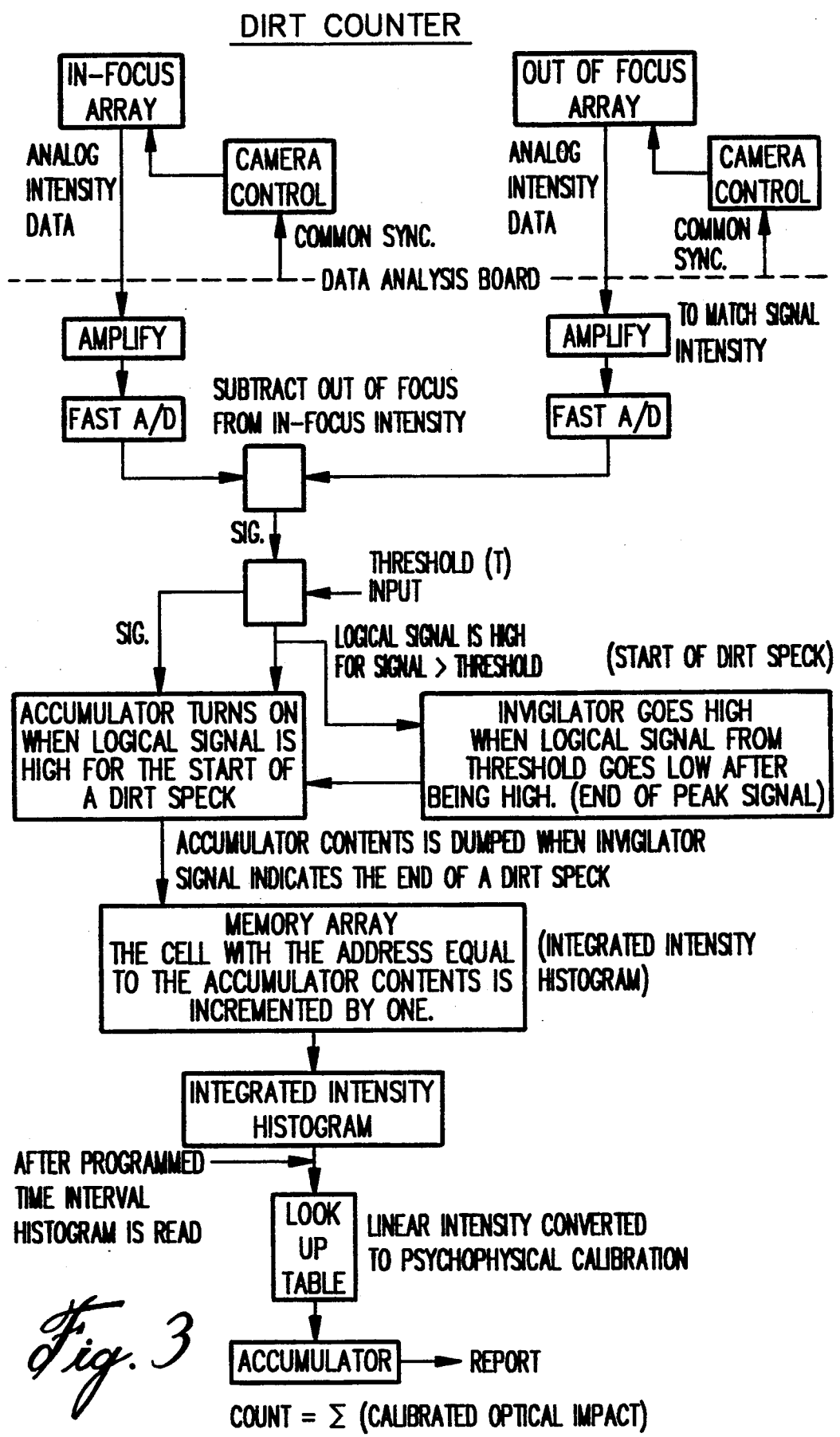
FIG. 3 is a flow chart of the process in accordance with the invention.

Turning now to FIG. 3, it can be seen that the two video signals are synchronized by using the same data clock and exposure control signals. The outputs of the in-focus array and out-of-focus array are amplified, and the amplified signals are then converted to digital signals. The out-of-focus digital value is then subtracted from the in-focus digital value, and the difference signal is then compared with a program threshold signal. If the difference signal exceeds the threshold signal, then a logical signal is fed to an accumulator to activate the accumulator. The signal is also fed to an invigulator. The difference digital signal is sent to the accumulator which, being enabled, computes the sum of consecutive array elements of high difference values, i.e., it performs the integration step.

When the difference signal falls to a value lower than the threshold signal, the invigulator will turn off the accumulator. The values in the accumulator are stored in the processor memory array and an integrated intensity histogram as well as other statistical data of each measured dirt speck is formed. The histogram may be read at program timed intervals or at program paper area coverages.

The integrated values are then converted into their corresponding sizes using a predetermined look-up table, and the size data is accumulated in a second accumulator. It is now possible to receive reports, for example, histograms, in terms of size rather than in terms of integrated values.

As will be apparent, it is also possible to use the data to stop the paper movement on detection of speck sizes exceeding predetermined thresholds of, for example, size and intensity.

Figure 4:
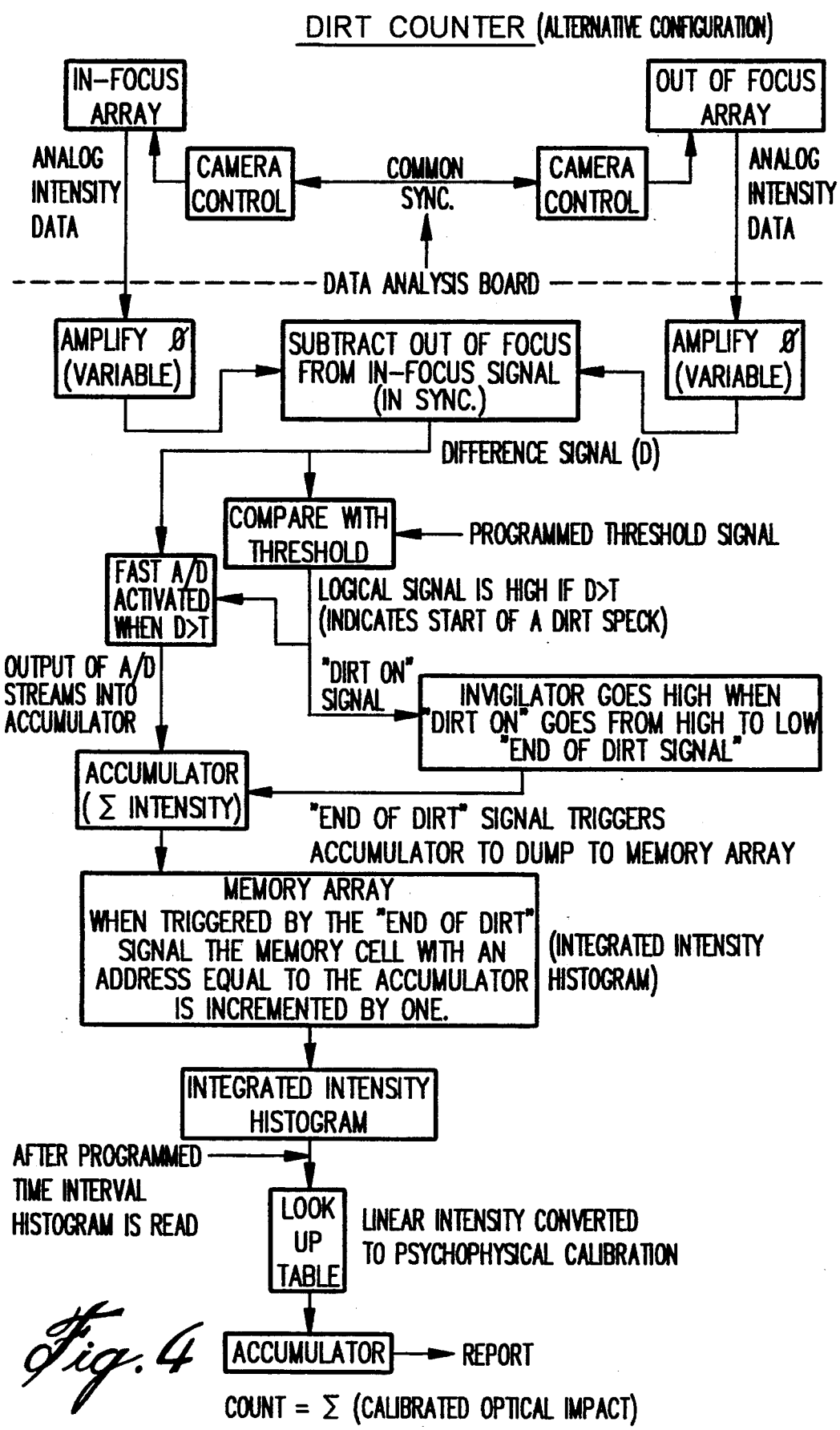
FIG. 4 is a flow chart of an alternate process.

As can be seen, the FIG. 4 process is very similar to the FIG. 3 process except that the subtraction is performed while the in-focus and out-of-focus signals are still in their analog state. The difference analog signal is then compared with a program threshold analog signal. In all other respects, the process as illustrated in FIG. 4 is the same as the process as illustrated in FIG. 3.

Although specific embodiments have been described, this was for the purpose of illustrating, but not limiting, the invention. Various modifications, which will come readily to the mind of one skilled in the art, are within the scope of the invention as defined in the appended claims.

We claim:

1. An on-line dirt counter for measuring and recording dirt speck sizes and intensities which appear on a first surface of a web of moving paper, comprising:
   a light source spaced from said first surface of said web of moving paper for directing a beam of light at said first surface of said web of moving paper, said beam of light being substantially diffusely reflected from said first surface of said web of moving paper;
   an in-focus sensor means including first focussing means and a first detector placed at an in-focus position to receive a first part of said reflected beam emitted at an angle with respect to said surface, and to provide an in-focus magnitude signal having an in-focus magnitude proportional to the magnitude of the light intensity of said first part;
   an out-of-focus sensor means including second focussing means and a second detector having a same aperture as said first detector placed at an out-of-focus position to receive a second part of said reflected beam emitted substantially at said angle with respect to said surface, and to provide an out-of-focus magnitude signal having an out-of-focus magnitude proportional to the magnitude of the light intensity of said second part;
   means for subtracting said out-of-focus magnitude from said in-focus magnitude to provide a difference magnitude;
   comparator means for comparing said difference magnitude to a threshold magnitude; and
   means for storing the occurrences and magnitudes of said difference magnitude on all occasions when said difference magnitude is greater than said threshold magnitude.

2. A dirt counter as defined in claim 1, further comprising a beam splitter spaced from said first surface of said web of moving paper to receive said reflected beam of light substantially normally with respect to said first surface and to split said reflected beam into said first and said second parts.

3. A dirt counter as defined in claim 2 wherein said means for storing comprises an accumulator having a signal input terminal and a control input terminal;
said difference magnitude being fed to said signal input terminal;
an enabling signal being fed to said control terminal when said difference magnitude exceeds said threshold magnitude;
whereby, said difference magnitude is stored in said accumulator when said difference magnitude exceeds said threshold magnitude.

4. A dirt counter as defined in claim 3 and including means for calculating integrated intensities from said stored difference magnitudes and for forming an integrated intensity histogram for each detected speck, indicative of the size and intensity of each speck, from said integrated intensities.

5. A dirt counter as defined in claim 4 and including look-up table means for converting said integrated intensities to corresponding sizes, and to form corresponding size histograms.

6. A dirt counter as defined in claim 4 wherein said means for calculating, said means for forming histograms and said look-up table comprise processor means.

7. A dirt counter as defined in claim 6 wherein said first surface of said web of moving paper comprises the top surface of said web of moving paper;
said beam of light being reflected upwardly from said top surface of said web of moving paper;
and further including:
light guide means disposed above said top surface of said web of moving paper to receive said reflected light beam;
lens means disposed above said light guide means, said reflected beam being directed to said lens means to be focussed thereby;
said lens means directing said focus beam to said beam splitter.

8. A dirt counter as defined in claim 7 wherein said first direction is parallel to said top surface of said web of moving paper;
said second direction is perpendicular to said top surface of said web of moving paper;
said in-focus sensor means comprising a linear array charge couple device; and
said out-of-focus sensor means comprising a linear array charge couple device.

9. A dirt counter as defined in claim 8 and further comprising;
a first top stabilizer plate;
a second bottom stabilizer plate defining a space between said first and second stabilizer plates;
said web of moving paper moving through said space between said stabilizer plates;
an opening in said top stabilizer plate through which said beam of light from said light source is directed at said top surface of said web of moving paper.

10. A dirt counter as defined in claim 9 wherein said in-focus sensor means is supported by an in-focus sensor means support plate, and wherein said out-of-focus sensor means is supported by an out-of-focus sensor means support plate.

11. A method for measuring and recording dirt speck sizes and intensities which appear on a first surface of a web of moving paper, comprising:
directing a beam of light from a light source at said first surface of said web of moving paper, said beam of light being reflected substantially diffusely from said first surface of said web of moving paper;
focusing and receiving a first part of said reflected beam emitted at an angle with respect to said surface in an in-focus sensor means placed at an in-focus position to provide an in-focus magnitude signal having an in-focus magnitude proportional to the magnitude of the light intensity of said first part of said beam;
focusing and receiving a second part of said reflected beam emitted substantially at said angle with respect to said surface in an out-of-focus sensor means having a same aperture as said in-focus sensor means and being placed at an out-of-focus position to provide an out-of-focus magnitude signal having an out-of-focus magnitude proportional to the magnitude of the light intensity of said second part of said beam;
subtracting said out-of-focus magnitude from said in-focus magnitude to provide a difference magnitude;
comparing said difference magnitude to a threshold magnitude; and
storing the occurrences and magnitudes of said difference magnitudes on all occasions when said difference magnitude is greater than said threshold magnitude.

12. A method as defined in claim 11, further comprising a step of splitting said reflected beam of light in a beam splitter to provide said first part of said beam and said second part of said beam respectively, said beam splitter receiving said beam substantially normally with respect to said first surface.

13. A method as defined in claim 12 wherein the stored occurrences of said difference magnitude are stored in an accumulator which has a signal input terminal and a control input terminal;
the difference magnitude being fed to the signal input terminal;
an enabling signal being fed to the control input terminal when the difference magnitude exceeds the threshold magnitude;
whereby, said difference magnitude is stored in said accumulator when said difference magnitude exceeds said threshold magnitude.

14. A method as defined in claim 13 and including the step of calculating integrated intensities from said stored difference magnitudes and for forming an integrated intensity histogram for each detected speck, indicative of the size and intensity of each speck, from said integrated intensities.

15. A method as defined in claim 14 and including the step of converting said integrated intensities to corresponding sizes using look-up table means, and to then forming corresponding size histograms.

16. A method as defined in claim 15 wherein said calculating, said histogram forming, and said look-up table means step are performed in processor means.

17. A method as defined in claim 16 wherein said first surface of said web of moving paper comprises the top surface of said web of moving paper;
said beam of light being reflected upwardly from said top surface of said web of moving paper;
said beam of light being guided by light guide means above said top surface of said web of moving paper to lens means diposed above said light guide means, said lens means focussing said beam of light;
said focussed beams being directed by said lens means to said beam splitter.

18. A method as defined in claim 17 wherein said web of moving paper moves through a space between stabilizer plates and is guided by said stabilizer plates.

* * * * *